United States Patent [19]

Tsao et al.

[11] Patent Number: 5,298,182
[45] Date of Patent: Mar. 29, 1994

[54] RAPID OPHTHALMIC GLYCOL/LOWER ALKANOL CLEANING AND DISINFECTING SOLUTION AND METHOD

[75] Inventors: Fu-Pao Tsao, Lawrenceville; Susan A. Littlefield, Norcross; John H. Stone, Conyers, all of Ga.

[73] Assignee: Ciba-Geigy Corporation, Ardsley, N.Y.

[21] Appl. No.: 971,699

[22] Filed: Nov. 4, 1992

Related U.S. Application Data

[63] Continuation-in-part of Ser. No. 825,757, Jan. 23, 1992, abandoned, which is a continuation of Ser. No. 456,058, Dec. 21, 1989, abandoned, which is a continuation-in-part of Ser. No. 304,672, Jan. 31, 1989, abandoned.

[51] Int. Cl.$^5$ .......................... A61L 2/18; C11D 3/20; C11D 3/44; C11D 3/48
[52] U.S. Cl. ...................... 252/106; 134/26; 134/42; 252/153; 252/170; 252/171; 252/173; 252/545; 252/DIG. 5; 252/DIG. 13; 252/DIG. 14; 422/28; 514/839; 514/840
[58] Field of Search ............... 252/106, 107, 153, 170, 252/173, DIG. 5, DIG. 13, DIG. 14; 422/28; 514/839, 840; 134/26, 42

[56] References Cited

U.S. PATENT DOCUMENTS

| | | | |
|---|---|---|---|
| 3,694,365 | 9/1972 | Castner | 252/106 |
| 4,046,706 | 9/1977 | Krezanoski | 252/106 |
| 4,124,520 | 11/1978 | Schwalley et al. | 252/106 |
| 4,127,423 | 11/1978 | Rankin | 134/30 |
| 4,209,449 | 6/1980 | Mayhew et al. | 260/403 |
| 4,315,828 | 2/1982 | Church | 252/153 |
| 4,336,385 | 6/1982 | Mayhew et al. | 548/112 |
| 4,421,665 | 12/1983 | Lloyd et al. | 252/106 |
| 4,507,219 | 3/1985 | Hughes | 252/118 |
| 4,525,346 | 6/1985 | Stark | 424/80 |
| 4,543,200 | 9/1985 | Sherman | 252/106 |
| 4,655,957 | 4/1987 | Chromecek et al. | 252/174.23 |
| 4,784,790 | 11/1988 | Disch | 252/174.12 |
| 4,908,147 | 3/1990 | Tsao et al. | 252/106 |

FOREIGN PATENT DOCUMENTS

| | | | |
|---|---|---|---|
| 0001888 | 5/1979 | European Pat. Off. | |
| 209192 | 1/1987 | European Pat. Off. | A61L 2/18 |
| 2406439 | 10/1977 | France | A61K 7/48 |
| 718050 | 11/1954 | United Kingdom | |
| 1472084 | 4/1977 | United Kingdom | A61L 13/00 |
| 2003033 | 8/1977 | United Kingdom | A61L 13/00 |

*Primary Examiner*—Dennis Albrecht
*Attorney, Agent, or Firm*—Edward McC. Roberts; R. Scott Meece

[57] ABSTRACT

A contact lens polymer material cleaning and disinfecting solution has about 21% by weight of a $C_3$–$C_8$ alkylene glycol, about 16% by weight of a lower alkanol, and 5% by weight of an ophthalmic device material compatible surfactant, about 1% by weight of a pH adjusting or regulating agent, about 1% by weight of a tonicity builder, about 0.1% of a viscosity enhancing agent, and water.

6 Claims, No Drawings

RAPID OPHTHALMIC GLYCOL/LOWER ALKANOL CLEANING AND DISINFECTING SOLUTION AND METHOD

This application is a continuation-in-part of application Ser. No. 07/825,757, filed Jan. 23, 1992, which is a continuation of Ser. No. 07/456,058, filed Dec. 21, 1989, which is a continuation-in-part of Ser. No. 07/304,672 filed Jan. 31, 1989, all of which are now abandoned.

FIELD OF THE INVENTION

The present invention relates to the field of contact lens disinfection systems, especially solutions and suspensions, although it can be applied to any disinfection purpose where the system components are compatible with the materials being disinfected.

BACKGROUND OF THE INVENTION

Cleaning regimens for ophthalmic devices of various types differ significantly in the cleaning efficacy and their procedural complexity. The typical regimens are heat disinfection and chemical (i.e. cold) disinfection, which eliminate pathogens and enzymatic cleaning to remove stubbornly adhering protein. Loosely held proteins and other loosely held contaminants can typically be removed by rubbing alone.

While various combinations of these regimens are indicated for various types of contact lenses, frequently contact lens users are less than diligent, and sometimes downright negligent in their strict adherence to the recommended procedures. Hence, a simplified system for disinfection and general cleaning of contact lenses has been long sought after.

Additionally, many disinfection systems currently known are not compatible with a large number of different types of lenses. It has been observed that there is a great deal of consumer confusion, especially when brand loyalty is being sacrificed for price. While many system/lens combinations may be suitable, others may result in irreversibly fouling the lens requiring that it be discarded and a new lens purchased. Therefore, it has also been desirable to develop a single disinfection and cleaning system which is compatible with most, if not all, contact lens materials.

Still further, most known disinfection systems require substantial amounts of time to achieve the desired degree of disinfection. Many times, contact lens wearers, for whatever the reason, neglect to continue the regimen for a period sufficient to disinfect the lens properly. Therefore, it is essential to proper compliance that a very rapid disinfection system for contact lenses be developed.

Exemplary known disinfection systems include those disclosed in British Patents 2,003,033 and 1,472,084; and U.S. Pat. Nos. 4,525,346 and 4,127,423. Typical marketed cleaning and disinfection systems are Cooper Vision's Miraflow ® and Alcon's Preflex ®/Polyclens ®/Polyflex ® systems. However, each of these suffers from one or more of the problems set out above.

OBJECTS OF THE INVENTION

It is an object of the invention to provide an ophthalmic device, preferably contact lens, disinfection system which has a simple regimen. It is a further object of the invention to provide a disinfection system for ophthalmic devices which can be completed in a short time period, typically in a couple of minutes or less. It is another object of the invention to provide solutions to achieve the foregoing objects.

Still another object is to provide a solution and method for cleaning contact lenses, which, with minimal patient input, both cleans and disinfects the contact lenses.

It is yet another object of the invention to provide a solution for cleaning and disinfecting contact lenses which is compatible with a wide range of contact lens types.

A further object of the invention is to provide a cleaning and disinfection system for ophthalmic devices which can be easily utilized by the eye-care professional to clean and disinfect such devices between usages in successive examinations.

SUMMARY OF THE INVENTION

These and other important objects are realized by a disinfection and cleaning formulation for ophthalmic devices, preferably contact lenses, comprising:
1. a $C_{3-8}$ alkylene glycol;
2. an ocularly acceptable, ophthalmic device material compatible, surfactant;
3. a lower alkanol;
4. optionally a pH regulating agent;
5. optionally a tonicity builder;
6. optionally a viscosity builder; and
7. water.

The formulation of the invention both disinfects and cleans contact lenses and other ophthalmic device materials in a very short period of time; typically under three minutes.

The formulations within the invention can also be used in virtually any composition requiring rapid disinfection, low toxicity and low irritancy. While not limiting the scope of the composition utility, exemplary utilities include inclusion of the invention composition within: topical medical preparations, cosmetics, facial cleansers, disinfecting soaps such as surgical soaps, disinfecting shampoos and disinfecting cleaners for household and/or industrial use. The only limitation on the incorporation of the instant formulation in various products or using them for various purposes is that the ingredients of the present invention be compatible with the ingredients of the composition to which it is to be added as well as with the surfaces to which it will be applied.

DETAILED DESCRIPTION OF THE INVENTION

The instant invention is a formulation, preferably a hypertonic solution or suspension, more preferably a solution, which is primarily a cleaner of proteins and debris and both cleans and disinfects ophthalmic device materials, especially contact lenses, in a relatively short period of time; i.e. under about three minutes, preferably under about 1.5 minutes, more preferably under about one minute, still more preferably about 20 to about 40 seconds, most preferably about 30 seconds. The formulation will usually be of the following composition, but the fourth, fifth and sixth components are only optional:
1. a $C_{3-8}$ alkylene glycol;
2. an ocularly acceptable, ophthalmic device material compatible, surfactant;
3. a lower alkanol;
4. (optionally) a pH regulating agent;
5. (optionally) a tonicity builder;

6. (optionally) a viscosity builder; and 7. water. Other suitable solvents includes, for example, alcohol or other solvent which is acceptable for use in an ophthalmic product.

Without being bound to the theory presented, it is believed that the various components work in tandem so that cleaning and disinfecting is completed in a minimal amount of time. The glycol has a disinfectant property and a polymeric swelling property. The swelling which results partially cracks any encrustations on the surface and allows the formulation to better reach the subsurface area of the material being disinfected thereby allowing for better disinfection and cleaning. The surfactant, is primarily a cleaner of proteins. However, it has a slight antimicrobial contribution, especially when a quaternary amine is present at a low pH. The lower alkanol has an antimicrobial effect of its own. The pH regulator is present so as to avoid deleterious pH changes due to the other components and conditions of use to which one puts the invention. The tonicity builder is present to ensure that the tonicity of the solution is hypertonic. Hypertonicity has an antimicrobial effect all its own, and additionally, prevents the material which is being disinfected from excessively swelling. The viscosity builder is really present for aesthetic purposes and to more easily carry out the first step, i.e. rubbing the device surface with the formulation. The water, of course, is present as an ophthalmically acceptable carrier for all of the other components.

The invention method is a regimen of rubbing a few drops of the formulation on the surface of the device and one rubs it for 5-30 seconds on each surface. The device is then rinsed for at least 5 seconds with normal saline and stored in normal saline for at least 20 seconds, after which the device can be reused. When used as part of other non-ophthalmic device cleaning compositions, the composition of the instant invention is incorporated into an appropriate formulation as set forth above and applied in the normal course to a normal surface for that type of formulation. Slight rubbing of the formulation on the surface may be employed, but may not be necessary depending upon the performance of the formulation's other ingredients. After application and optional rubbing, rinsing with saline (if tonicity need be maintained) or water (if tonicity is not critical) completes the operation. Where the instant formulation is used alone, it is applied in the normal manner as any other cleaner or disinfectant to the compatible surface, rubbed slightly for 5-30 seconds and rinsed with normal saline or water as appropriate for the purpose for which the composition is being used.

In the typical formulation of the invention, the $C_{3-8}$ alkylene glycol is present from about 10% to about 50% by weight, preferably about 15% to about 40% by weight, still more preferably about 17% to about 25% by weight, most preferably about 21% by weight of the entire formulation.

The $C_{3-8}$ alkylene glycol is preferably selected from 1,2 or alpha, omega glycols such as 1,2-propylene glycol, 1,2-butylene glycol, 1,2-pentylene glycol, 1,2-hexylene glycol, 1,3-propylene glycol, 1,4-butylene glycol, 1,5-pentylene glycol, and 1,6-hexylene glycol. Also preferably, the $C_{3-8}$ alkylene glycols are $C_3$ or $C_4$ alkylene glycols such as 1,2-propylene glycol, 1,3-propylene glycol, 1,2-butylene glycol, 1,3-butylene glycol, 1,4-butylene, 2,3-butylene glycol, 2-methyl-1,2-propylene glycol, and 2-methyl-1,3-propylene glycol. Most preferably, the $C_{3-8}$ alkylene glycol is 1,2-propylene glycol or 1,3-propylene glycol. 1,6-Hexylene glycol is also preferred.

The surfactant may be present from about 0.5% up to about 25% by weight, but usually is present in an amount of about 2% to about 15% by weight, preferably about 3% to about 12% by weight, most preferably about 5% by weight to about 10% by weight of the entire formulation. The surfactant is selected from virtually any ocularly acceptable surfactant including nonionic, anionic, and amphoteric surfactants, but is preferably selected from a) compounds of formula I $$(AmSur-O)_3-P=O \qquad (I)$$

wherein the group AmSur is of the formula

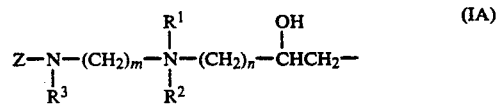

$$(IA)$$

wherein each of $R^1$–$R^3$ is independently lower alkyl, hydroxy lower alkyl, or carboxy lower alkyl, Z is an alkanoyl of 6-18 carbon atoms or Z together with one of $R^1$ and $R^3$ is methylene substituted by $C_5$–$C_{17}$ alkyl; n and m are each independently 1–4. Where AmSur contains a net charge, a suitable ocularly acceptable counter ion, such as chloride, is also present in an appropriate amount. The three AmSur radicals can be the same or different, but preferably all three AmSur radicals in one molecule are the same;

b) compounds of the formula

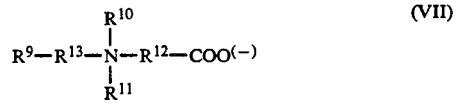

$$(VII)$$

wherein $R^9$ is alkyl of 5-17 carbon atoms or a $C_{6-20}$ alkanoylamino; each of $R^{10}$ and $R^{11}$ is independently lower alkyl, hydroxy lower alkyl, or carboxy lower alkyl; $R^{12}$ is an alpha, omega-alkylene of 1 to 6 carbons which is unsubstituted or substituted by lower alkyl, hydroxy, or hydroxy lower alkyl; and $R^{13}$ is alpha, omega-$C_1$–$C_5$ alkylene;

c) compounds of the formula

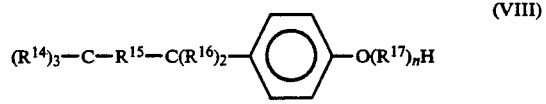

$$(VIII)$$

wherein each $R^{14}$ and each $R^{16}$ is independently $C_{1-4}$ alkyl; $R^{15}$ is $C_{1-4}$ alpha, omega-alkylene; each $R^{17}$ is independently $$-CH_2CH_2O-,\ -CH_2CH_2CH_2O-,\ \text{or}$$

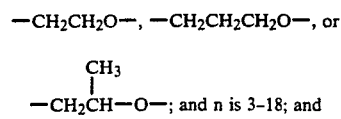

and n is 3-18; and d) compounds of the formula

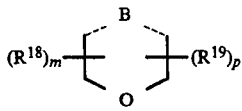

wherein B is a $C_{1-4}$-alpha, omega-alkylene; p is an integer 0 to d-1; m is an integer of from 0 to (d-p-1); d=4-7; each $R^{18}$ is independently H or a $C_{1-4}$ alkyl which is unsubstituted or substituted by at least one $R^{19}$; each $R^{19}$ is independently a hydroxy which is free, etherified by $R^{20}$, or esterified by $R^{21}$; each $R^{20}$ is a $C_{2-4}$ straight or branched oxyalkylene orpoly($C_{2-4}$ straight or branched oxyalkylene), the terminal oxygen of which is bound to H or $R^{21}$; and each $R^{21}$ is independently an acyl of a $C_{2-24}$ alkanoic acid or a $C_{4-24}$ alkenoic acid; provided that in each compound of the formula IX there is at least one free hydroxy group, and at least one $R^{21}$ group. Compounds of formula VII are typically available from Miranol under the names Mirataine ® and Miranol ®; compounds of the formula VIII are available under the names Igepal CA ®, Polytergent ® and Triton X ®; and compounds of formula IX are available under the Span ® and Tween ® brand names.

Preferably the compounds of Formula I are selected from

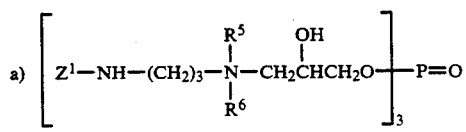

wherein $R^5$ and $R^6$ are each $C_1$-$C_4$ alkyl and $Z^1$ is $C_6$-$C_{18}$ alkanoyl;

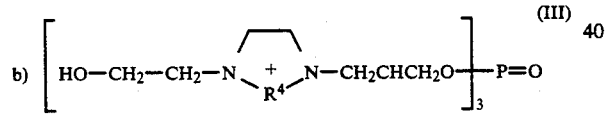

wherein $R^4$ is methylene substituted by $C_5$-$C_{17}$ alkyl; and

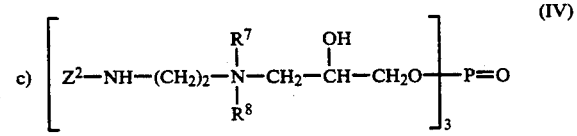

wherein $Z^2$ is $C_{12}$-$C_{14}$ alkyl, one of $R^7$ and $R^8$ is carboxy lower alkyl, and the other of $R^7$ and $R^8$ is hydroxy lower alkyl.

Compounds of formulae II-IV are available from Mona Industries, New Jersey under the series trade name Monaquat ®-P. More preferably, within formulae II-IV, are the compounds

wherein $Z^2$ is $C_6$-$C_{17}$ alkanoyl (available under the name Monaquat ®P-TC) or $C_{12}$-$C_{14}$ alkanoyl (available under the name Monaquat ®P-TD);

b) compounds of formula III, available under the name Monaquat ®P-TZ; and

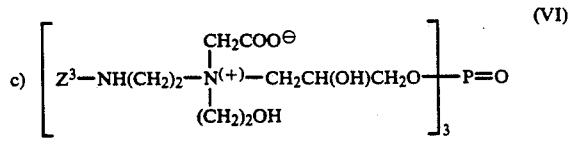

wherein $Z^3$ is $C_{12}$-$C_{14}$ alkanoyl, available under the name Monaquat ®P-TL. The most preferable compound of the Monaquat ®P series for use in the instant invention is Monaquat ®P-TL, i.e. compounds of formula VI. Compounds within formula II generally are disclosed in U.S. Pat. Nos. 4,209,449 and 4,336,385, the disclosure of which are included herein by reference.

Another preferred class of surfactants includes poloxamers, reverse poloxamers, meroxapols as Pluronic 10R5, 10R8, 17R1, 17R2, 17R4, 17R8, 25R1, 25R2, 25R4, 25R5, 25R8, 31R1, 31R2 and 31R4, all available from BASF Wyandotte Corp.), poloxamines, polyethyleneglycols, polypropyleneglycols, polypropyleneglycol-buteths (such as Pluracol W170, W260, W660, W2000, W3520N, and W5100N, available from BASF Wyandotte Corp., Parsippany, N.J.), polypropyleneglycol oleates, polypropylene-pareths (such as Plurafac D-25 from BASF Wyandotte or other linear alcohol alkoxylates), tetrahydroxypropylethylenediamine, ceteareths (such as Plurafac A-38 and Plurafac A-39 from BASF Wyandotte Corp.), NTA disodium ethylenediamonotetraacetrate salts, EDTA (nitrolotriacetic acid) salts, and pentetate salts (such as diethylenetriamine pentaacetic acid sodium salt) Within this group, especially useful are:

poloxamers 101 (such as Pluronic L-31 Polyol from BASF Wyandotte Corp.), 105, 108 122, 123, 124, 181, 182, 183, 184, 185, 188, 212, 215, 217, 231, 234, 235, 237, 238, 282, 288, 331, 333, 334, 335, 338, 401 (such as Pluronic L-121 Polyol from BASF Wyandotte Corp.), 402, 403, and 407;

meroxapols 105, 108, 171, 172, 174, 178, 251, 252, 254, 255, 258, 311, 312, and 314;

poloxamines 304, 504, 701, 702, 704, 707, 901, 904, 908, 1101, 1102, 1104, 1107, 1301, 1302, 1304, 1307, 1501, 1502, 1504, and 1508;

polyethylene glycols selected from PEGs 4, 6, 8, 12, 20, 32, 40, 75, 150, and PEG 6 methyl ether; polypropylene glycols selected from PPGs 9, 12, 17, 26, and 30;

polypropylene glycol-buteths selected from ppg-5-buteth-7, ppg-7-buteth-10, ppg-12-buteth-16, ppg-20-buteth-30, ppg-28-buteth-35, and ppg-33-buteth-45;

ppg-26-oleate;

ppg-6-pareth;

tetrahydroxypropylethylenediamine;

ceteareth 27 and 55;

trisodium NTA;

trisodium EDTA and tetrasodium EDTA;

EDTA; and pentasodium pentetate. Each of these compounds can be found in the C.T.F.A Ingredient Dictionary.

The lower alkanol is present up to 50% by weight, but usually from about 2% to about 30% by weight, preferably about 10% to about 20% by weight, most preferably about 16% by weight of the entire formulation. Lower alkanol is selected from $C_{1-7}$, preferably $C_{1-4}$, straight or branched alkanols, such as methanol, ethanol, n-propanol, isopropanol, n-butanol, sec-butanol and t-butanol, more preferably isopropnnol or ethanol, most preferably isopropanol.

The pH regulating component can be added as a preformed buffer or can be formed in situ. If the pH of the solution without this component is suitable it is not required, although its presence is desirable. Any ocularly compatible inorganic or organic acid or base or organic buffer system can be used. Typical buffer systems include the well known phosphate or borate systems. Other suitable systems include, without limitation, the lactate, pyruvate, citrate, tartrate, acetate, and laurate systems.

The pH of the final solution may be advantageously in the range of 3-7.0, preferably 5-7, more preferably about 5.5 to about 6. The lower pHs, while suitable, are advantageous in that minimum disinfecting time is shortened over the same composition at higher pH, but disadvantageous in that reestablishment of neutral pH is necessary before a lens is placed back on the eye.

Most preferably the buffer system used will have a pK in the range of the desired pH range so as to maximize the buffering capacity. The most preferable buffer system is lactic acid/lactate which is preferably formed in situ by the addition of lactic acid alone. In the case of lactic acid/lactate as the pH adjuster (i.e. buffer), the combined lactic acid and lactate are preferably present from about 0.5-about 2% by weight of the solution based on lactate ion, more preferably about 0.75% to about 1.5%, most preferably about 1.1% of the solution.

The tonicity builder, when present, is typically present in an amount which yields a tonicity for the invention solution equivalent to sodium chloride solutions in the range of 0.5 up to but less than 5% sodium chloride, preferably up to 2% sodium chloride, still more preferably in the range of 0.75 to 1.5% sodium chloride, more preferably about 0.9 to 1.1% sodium chloride, most preferably about 1% sodium chloride, all percentages being w/v. The most preferable compound for use as a tonicity builder is sodium chloride, although any ocularly compatible inorganic or organic salt which does not interfere with the other components will do. For example, excess lactic acid and lactate salt may be used to enhance the buffering capacity and simultaneously contribute sufficiently to the tonicity that a tonicity builder is not necessary or desired. Hence, the tonicity builder can be absent entirely or present up to an amount equivalent in tonicity with just under 5% sodium chloride.

The overall solution tonicity should preferably be hypertonic, preferably at least equivalent to 1.1% NaCl. It should not be less than isotonic. The tonicity builder amounts stated above can be adjusted by those of ordinary skill to have the solution meet these overall more preferable limits. Typical tonicity builders include ophthalmically acceptable alkaline metal or alkaline earth metal halide, phosphate, carbonate, sulfate, etc.

The viscosity enhancer is present to help increase the solution viscosity to preferably not greater than 100 cps, more preferably not greater than 80 cps, still more preferably not greater than 30 cps, most preferably not greater than 10 cps. Any ocularly compatible non-ionic or quaternary ammonium viscosity enhancer is suitable. Examples of non-ionic viscosity enhancers utilizable on the instant invention include: lower alkyl celluloses (i.e. methyl cellulose, ethyl cellulose, etc.) hydroxy lower alkyl celluloses (i.e. hydroxy methyl cellulose, hydroxy ethyl cellulose, hydroxy propyl cellulose, etc.), poloxamers, reverse poloxamers, ethoxylated ethylene diamines, etc. Exemplary quaternary ammonium viscosity enhancer includes:

Preferably, the viscosity enhancer is a cellulose ether, more preferably hydroxy lower alkyl cellulose, most preferably hydroxy ethyl cellulose, such as HECQP 4400 available from Union Carbide. In a most preferred solution, hydroxy ethyl cellulose is the viscosity enhancer and is present in an amount of about 0.1% by weight of the solution.

Another preferred class of viscosity enhancing agents includes poloxamers, reverse poloxamers, meroxapols, poloxamines, polethyleneglycols, polypropyleneglycols, polypropyleneglycol-buteths, polypropyleneglycol oleates, polypropylene-pareths, tetrahydroxypropylethylenediamine, cetearethds, NTA salts, EDTA salts, and pentetate salts. Within this group, especially useful are:

poloxamers 101, 105, 108 122, 123, 124, 181, 182, 183, 184, 185, 188, 212, 215, 217, 231, 234, 235, 237, 238, 282, 288, 331, 333, 334, 335, 338, 401, 402, 403, and 407;

meroxapols 105, 108, 171, 172, 174, 178, 251, 252, 254, 255, 258, 311, 312, and 314;

poloxamines 304, 504, 701, 702, 704, 707, 901, 904, 908, 1101, 1102, 1104, 1107, 1301, 1302, 1304, 1307, 1501, 1502, 1504, and 1508;

polyethylene glycols selected from PEGs 4, 6, 8, 12, 20, 32, 40, 75, 150, and PEG 6 methyl ether; polypropylene glycols selected from PPGs 9, 12, 17, 26, and 30;

polypropylene glycol-buteths selected from ppg-5-buteth-7, ppg-7-buteth-10, ppg-12-buteth-16, ppg-20-buteth-30, ppg-28-buteth-35, and ppg-33-buteth-45;

ppg-26-oleate;

ppg-6-pareth;

tetrahydroxypropylethylenediamine;

ceteareth 27 and 55;

trisodium NTA;

trisodium EDTA and tetrasodium EDTA;

EDTA; and pentasodium pentetate. Each of these compounds can be found in the C.T.F.A Ingredient Dictionary. The surfactant and viscosity agent may be the same.

The solution of the invention can be formulated from the above components in any manner known in the art. For example, the solid components can be dissolved directly in the water, either simultaneously or sequentially, with liquid components being added thereto either before or after the solid components. Alternatively, the solid components can be triturated with one or more non-water liquid components and this mixture diluted with an appropriate amount of water. It is preferable to dissolve all of the components (other than the viscosity enhancer) first and then mix the viscosity enhancer into this solution.

A single entity may serve as both surfactant and viscosity enhance and if so, its presence must be within the limits set forth for each component. Of course, if two enhancers or surfactants are present and one has both properties, that single entity is included with each of the two types of materials for determining adherence to the invention limits. Variations of the above will be apparent to the ordinarily skilled formulator.

The instant solutions are rapid cleaning and disinfecting solutions for a wide range of contact lens materials. Typically, one applies a few drops of the solution to the lens material and rubs it for 5-30 seconds, preferably 10-20 seconds, more preferably about 15 seconds. This is repeated for the opposite surface. The lens is then rinsed in normal saline for at least 5 seconds, preferably 10-20 seconds, most preferably 15 seconds, and stored in normal saline for at least 20 seconds, preferably 30 seconds to 1.5 minutes, most preferably 1 minute. Longer storing times are acceptable, but not necessary. The instant solution can be used in the above method for all types of contact lenses; soft lenses, hard lenses, and rigid gas permeable lenses. Such lens materials for which the instant solution can be used include bufilcon A, cobufocon A, crofilcon A, deltafilcon A, deltafilcon B, dimefilcon A, droxifilcon, etafilcon A, hefilcon A, hefilcon B, itafocon A, lidofilcon A, mafilcon A, ocufilcon A, ocufilcon B, optacryl 60, pasifocon A, pasifocon B, pasifocon C, perfilcon A, phemfilcon A, polymacon, porofocon B, silafilcon A, silafocon A, tefilcon, tetrafilcon A, vifilcon A, PMMA, silicone/MMA copolymer, MMA/glyceryl methacrylate copolymer, and poly t-butyl stryene. Others will be apparent to those of ordinary skill.

Having fully described the invention, the following Examples are presented to exemplify but do not limit the invention.

EXAMPLE 1

21 grams propylene glycol, 5 grams Monaquat®P-TL having the formula

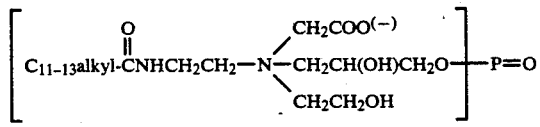

16 grams isopropyl alcohol, 1.5 grams of 85% [weight/volume] lactic acid, 1.1 grams sodium chloride, and 0.11 grams of hydroxy ethyl cellulose are dissolved in 55 mls of deionized water, and the pH is adjusted with 5M NaOH to result in a solution of the invention having a pH of 5.0.

Example 2

10.5 g Propylene glycol, 6 g Monoquat®P-TL (see Example 1), 16 g isopropyl alcohol, 1.0 g tartaric acid, 1.0 g sodium chloride and 0.1 g HECQP ™ 4400 (hydroxyethyl cellulose) are dissolved in 54 g of deionized water and the pH adjusted to 5.0 with 5M NaOH.

Examples 3-16

The following examples were prepared according to Example 1, except that the components set forth and in the amounts in the table below were used. Water was used to bring the total weight up to 100%.

| | Propylene glycol (g) | Surfactant | Isopropyl Alcohol (g) | Organic Acid | NaCl | Hydroxyethyl Cellulose | pH |
|---|---|---|---|---|---|---|---|
| 3 | 10.5 | Monoquat P-TL 6 g | 16 | Tartaric 1 g | 0.5 g | 0.1 g | 5.5 |
| 4 | 20 | Monoquat P-TL 6 g | 16 | Tartaric 1 g | 0.5 g | 0.1 g | 5.5 |
| 5 | 10.5 | Monoquat P-TL 6 g | 16 | Tartaric 1 g | 0.5 g | — | 5.5 |
| 6 | 30 | Monoquat P-TL 6 g | 16 | Tartaric 1 g | 0.5 g | — | 5.5 |
| 7 | 30 | Monoquat P-TL 6 g | 8 | Tartaric 1 g | 0.5 g | — | 5.5 |
| 8 | 30 | Monpquat P-TL 6 g | 8 | Tartaric 1 g | 0.5 g | — | 5.0 |
| 9 | 30 | Monoquat P-TL 6 g | 16 | Tartaric 1 g | 0.5 g | 0.1 g | 5.5 |
| 10 | 10.5 | Monoquat P-TL 6 g | 8 | Lactic 1.1 g | 0.8 g | 0.11 g | 5.0 |
| 11 | 30 | Monoquat P-TL 6 g | 8 | Tartaric 2 g | 0.5 g | 0.1 g | 5.5 |
| 12 | 30 | Monoquat P-TL 6 g | 8 | Lauric 0.0125 g | 0.5 g | 0.1 g | 5.5 |
| 13 | 21 | Monoquat P-TL 5 g | 16 | Lactic Acid 1.5 g | 1.1 g | 0.11 g | 5.0 |
| 14 | 20 | Tween 20 20 g | 16 | Lactic Acid 1.2 g | 1.0 g | 0.10 g | 5.0 |
| 15 | 20 | Triton X-100 2 g | 16 | Lactic Acid 1.2 g | 1.0 g | 0.10 g | 5.0 |
| 16 | 21.8 | Tween 20 21.2 g | 16.4 | Lactic Acid 1.47 g | 1.0 g | — | 5.0 |

Examples 17-20

Examples 17-20 were prepared by dissolving in 49.3 g of water (deionized) isopropyl alcohol, hexylene glycol, and/or propylene glycol as stated in the Table below. In addition, 1 g of Pluronic L-31 was dissolved therein. 2 g of Lactic Acid were added to result in a solution having a pH of 3.0.

| Example | Hexylene Glycol (g) | Isopropyl Alcohol (g) | Propylene Glycol (g) |
|---|---|---|---|
| 17 | 30 | 40 | 0 |
| 18 | 30 | 30 | 10 |
| 19 | 20 | 40 | 10 |
| 20 | 10 | 50 | 10 |

Examples 21-24

Examples 21-24 were prepared according to Example 17 except that the Pluronic L-31 is replaced by 1.0 g of Betaine and the following amounts of hexylene glycol, isopropyl alcohol, and propylene glycol were used.

| Example | Hexylene Glycol (g) | Isopropyl Alcohol (g) | Propylene Glycol (g) |
|---------|---------------------|-----------------------|----------------------|
| 21 | 30 | 30 | 0 |
| 22 | 30 | 40 | 0 |
| 23 | 20 | 50 | 0 |
| 24 | 20 | 40 | 10 |

Example 25

Solutions of the Examples set forth below ere tested for effectiveness against Acanthamoeba cysts as follows:

A $10^7$ cyst pellet was dissolved in 10 ml of test solution to result in a $10^6$ cyst/ml concentration in test solution. At the times specified below, 1 ml was withdrawn and diluted with 49 ml of saline to result in a cyst concentration of $2 \times 10^4$ cyst/ml. 0.1 Ml of this diluted solution was then added to 10 ml of nutrient media so that the entire nutrient media began with a $2 \times 10^3$ cyst population. The innoculated nutrient media were cultured for 3 weeks at which point effectiveness was assessed as (a) total kill (−) or (b) partial or no kill (+). The results are reported in the Table below.

| Solution Example No. | Exposure Time (min.) 1 | 5 |
|---|---|---|
| 17 | + | − |
| 18 | + | − |
| 19 | + | − |
| 20 | + | − |
| 21 | + | − |
| 22 | + | − |
| 23 | + | − |
| 24 | + | − |

I claim:

1. A contact lens polymer material cleaning and disinfecting solution comprising:
   a) about 21% by weight of a $C_3$–$C_8$ alkylene glycol,
   b) about 16% by weight of a lower alkanol,
   c) about 5% by weight of an ophthalmic device material compatible surfactant,
   d) about 1% by weight of a pH adjusting or regulating agent,
   e) about 1% by weight of a tonicity builder,
   f) about 0.1% of a viscosity enhancing agent, and
   g) the balance water.

2. A method of disinfecting and cleaning a contact lens polymer material comprising rubbing the surface of said polymer material with an effective disinfecting and cleaning amount of a solution of claim 1, followed by rinsing said polymer material with normal saline.

3. The method of claim 2 wherein each surface of said polymer material is rubbed with said solution for about 15 seconds and then the entire polymer material is rinsed with normal saline for 10 seconds.

4. The method of claim 3 wherein said polymer material is in the form of a contact lens.

5. The method of claim 3 wherein said rinsing step is followed by storing said polymer material in normal saline for about 1 minute.

6. A method of disinfecting and cleaning a contact lens polymer material comprising rubbing the surface of said polymer material with an effective disinfecting and cleaning amount of a solution of claim 1, followed by rinsing said polymer with normal saline.

* * * * *